United States Patent [19]
Shinmen et al.

[11] Patent Number: 4,737,460
[45] Date of Patent: Apr. 12, 1988

[54] PEROXIDASE AND A PROCESS OF ITS PREPARATION

[75] Inventors: Yoshifumi Shinmen, Kyoto; Sumio Asami; Norihide Amano, both of Osaka; Teruo Amachi, Hyogo; Hajime Yoshizumi, Osaka; Eiichi Kosugi, Tokyo, all of Japan

[73] Assignee: Suntory Limited, Osaka, Japan

[21] Appl. No.: 762,838

[22] Filed: Aug. 6, 1985

[30] Foreign Application Priority Data

Aug. 7, 1984 [JP] Japan ................ 59-165400

[51] Int. Cl.$^4$ ............ C12N 9/08; C12Q 1/28; C12R 1/645
[52] U.S. Cl. .............. 435/192; 435/28; 435/911
[58] Field of Search .................. 435/192, 28

[56] References Cited

U.S. PATENT DOCUMENTS 4,328,312  5/1982  Tsurumi et al. ............ 435/192

FOREIGN PATENT DOCUMENTS 57-99192   6/1982  Japan ................ 435/192
59-179075 10/1984  Japan ................ 435/192

OTHER PUBLICATIONS

Ross, Biologi of the Fungi, 1979, pp. 129–136.
Agric. Biol. Chem., vol. 45, No. 5, pp. 1297–1299 (1981).
Chemical Abstracts, vol. 100, No. 13, p. 509 (Mar. 1984), abstract No. 101626x.

Primary Examiner—Lionel M. Shapiro
Attorney, Agent, or Firm—Cushman, Darby & Cushman

[57] ABSTRACT

A novel peroxidase that is non specific and that does not contain isozymes and hence, is suitable as a diagnostic reagent or as a marker enzyme in enzyme immunoassay is provided as well as a process of its preparation. The novel peroxidase is produced by a microorganism of a new genus Arthromyces.

3 Claims, 1 Drawing Sheet

PEROXIDASE AND A PROCESS OF ITS PREPARATION

BACKGROUND OF THE INVENTION

1. Field of the Invention:

The present invention relates to a microbiological process for producing peroxidase. More particularly, the invention relates to a process for producing a novel peroxidase from a microorganism of a new genus Arthromyces that develops color with the aid of a hydrogen donor such as a 4-amino-antipyrine (hereunder abbreviated as 4-AA)-phenol system, a 3-methyl-2-benzothiazolinone hydrazone (hereunder MBTH)-diethylaniline (hereunder DEA) system, and a 2,2'-azino-di(3-ethylbenzothiazoline)-6-sulfonic acid (hereunder ABTS).

2. Prior Art:

Peroxidase is an enzyme that oxidizes a variety of compounds in the presence of hydrogen peroxide. Currently, peroxidase is used as a clinical or diagnostic reagent in combination with a variety of oxidases for the assay of glucose, cholesterol, phospholipids and uric acid. Another current use of peroxidase is as a marker enzyme in enzyme immunoassay. The only commercially available sources of peroxidase are plants such as horseradish and Japanese radish. Since the peroxidase originating from such plants contains isozymes of slightly different properties, they must be separated laboriously in order to obtain a pure form of peroxidase suitable for use as a diagnostic reagent.

Peroxidases originating from microorganisms are also known and they include Cytochrome $C_3$ peroxidase and NADH peroxidase produced from bacteria and fungi. However, these peroxidases are not non-specific as are the ordinary peroxidases derived from horseradish and Japanese radish, and such peroxidases specific to particular system are not suitable for use as clinical and diagnostic reagents. It has recently been reported that peroxidase using o-dianisidine as a hydrogen donor can be produced from $E.$ $coli$ or microorganisms of the genus Myrothecium. However, this peroxidase is also unsuitable as a diagnostic reagent since the use of o-dianisidine in clinical and diagnostic agents is increasingly discouraged because of its potential carcinogenic effects.

SUMMARY OF THE INVENTION

The present inventors made various efforts to obtain from fast growing microorganisms a peroxidase that is comparable to the conventional peroxidase derived from horseradish or Japanese radish in that it can be used either as a clinical or diagnostic reagent or as a marker enzyme in enzyme immunoassay. To attain this object, the inventors isolated a large number of naturally occurring microorganisms and examined their ability to produce peroxidase that develops color with the aid of a hydrogen donor such as a 4-AA-phenol system, MBTH-DEA system or ABTS. As a result, the inventors have found a strain of microorganism belonging to a new genus that produces peroxidase in a high yield. The present invention has been accomplished on the basis of this finding.

DETAILED DESCRIPTION OF THE INVENTION

Figure 1:
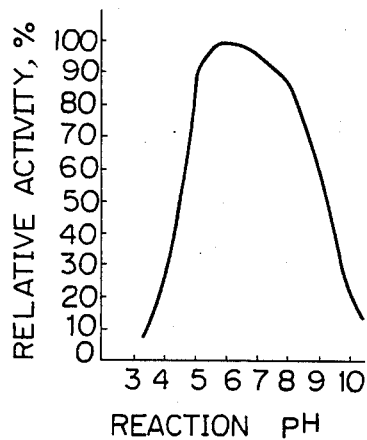
FIG. 1 is a graph showing the relationship between the reaction pH and the relative activity of the peroxidase of the present invention.

The strain disclosed by the present invention has the following mycological properties.

(1) State of growth on various media

Culture conditions: RT (25°–28° C.) under scattered light (i) Potato-glucose agar medium Colonies attained a diameter of 24–27 mm in 5 days. Short and dense aerial hyphae. White colonies. The reverse side of colonies was white to yellowish white. The hyphae were septate and branched. Occasional constrictions occurred at the septa. The surface of hyphae was smooth. Hyaline. Width of hyphae ranging from 2 to 5 μm. Formation of conidia observed. Chlamydospore-like cells observed. Such cells, either spherical or elliptical in shape, produced intercalary or at the terminal or on the side of hyphae. Diameter of such cells ranging from 5 to 9 μm or 10–15×6–10 μm. In about 14-day-old cultures, many sclerotia were produced. Sclerotia were either spherical or elliptical in shape and their color was brown to dark brown. Diameter of sclerotia ranging from 75–100 μm, or 100–175×75–100 μm.

(ii) Malt extract agar medium

Colonies attained a diameter of 7–12 mm in 5 days. Short and dense aerial hyphae. White colonies. The reverse side of colonies was also white. The hypae were septae and branched. Occasional constrictions occurred at the septa. The surface of hyphae was smooth. Width of hyphae ranging from 2 to 5 μm. No conidia was observed and only chlamydospore-like cells were observed. Such cells, either spherical or elliptical in shape, produced intercalary or at the terminal or on the side of hyphae. Diameter ranging from 8 to 13 μm, or 10–20-×5–12 μm.

(iii) YpSs medium

Colonies attained a diameter of 52–60 mm in 5 days. The colonies were white, so was their reverse side. Dense aerial hyphae. Very sparse aerial hyphae in the center of colonies. The hyphae were septate and branched. Occasional constrictions occurred at the septa. The surface of hyphae was smooth. Hyaline. Width ranging from 2 to 5 μm. Formation of conidia was observed.

(2) Microscopic examination

Smear preparations and slide cultures of the strain of the invention on several culture media were prepared for observation of the process of conidium formation and appearance of conidiophores and conidia.

Conidiophores are difficult to discern from vegetable hyphae. The process of conidium formation is of thallic type. The formation of conidium starts with the cutting off of the tip of the hypha from the base portion. The residual hypha is then fragmented either in the center or at the point slightly above the center to form a conidium. At the same time, a new shoot of a hypha arises from the side of the residual hypha immediately beneath the cut plane, and another conidium formed by the process just described. This process is repeated to form conidia, sometimes yielding a spherical cluster of conidia at the terminal of a hypha. The hypha arising from the side of the residual hypha immediately beneath the cut plane may sometimes continue to grow. The conidia are in the form of short cylindrical with rounded ends. Hyaline. The surface of conidia is smooth. Diameter in the range of 3.8–6.0×1.5–2.5 μm.

(3) Physiological properties

The pH range that enables the growth of the microorganism disclosed by the present invention is from 4 to 10, with the optimum range being 6–9. The growth temperature is in the range of 10°–45° C., with the optimum range being 30°–40° C.

Noting that the mycological properties of the microorganism disclosed by the present invention are characterized by the thallic type of conidiogenesis, the inventors referred to W. B. Kendrick and J. W. Carmichael, Hyphomycetes in "The Fungi, vol, IVA" (Ainsworth, G. C. et al eds.) and to J. W. Carmichael, W. B. Kendrick, I. L. Conners and L. Sigler, Genera of Hyphomycetes, for finding a genus to which the microorganism of interest would belong. However, the inventors were unable to locate a specific genus that included a microorganism having morphological characteristics identical with those of the strain of interest. The inventors therefore concluded that the strain would appropriately be classified as belonging to a new genus of Hyphomycetes. Hence, the inventors created a new genus, Arthromyces, and named the strain of interest *Arthromyces ramosus*. The genus Arthromyces is defined as follows:

Belongs to subdivision Deuteromycotina, class Hyphomycetes. The hypha is colorless, septate and branched. The conidiophore is difficult to discern from a vegetative hypha. The process of conidium formation is of the thallic type. The formation of a conidium starts with the cutting off of the tip of the hypha from the base portion, and the residual hypha is then fragmented to form a conidium. At the same time, a new hypha arises from the side of the residual hypha immediately beneath the cut plane, and another conidium forms by the same process. The conidium is short and cylindrical. Hyaline.

Type species: *Arthromyces ramosus* N. Amano, sp. nov.

The strain just described was isolated from the soil. *Arthromyces ramosus* was deposited with the Fermentation Research Institute, Agency of Industrial Science and Technology under FERM P-7754. It was transferred to a deposition under the Budapest Treaty on June 11, 1985 (International Deposition Acceptance No. FERM BP-838). The halotype specimen of *Arthromyces ramosus* has been kept in the mycological herbarium, Laboratories of Applied Microbiology, Research Center, Suntory Ltd.

The strain used in the present invention may be cultured by inoculating a liquid or solid medium with spores or mycelia from the strain or a liquid seed culture obtained by precultivation. A liquid medium may contain any common carbon sources such as glucose, fructose, xylose, saccharose, maltose, soluble starch, molasses, glycerol and mannitol. Usable nitrogen sources include naturally occurring substances such as peptone, yeast extract, malt extract, meat extract, casamino acids, and corn steep liquor, as well as organics such as urea, and inorganics such as sodium nitrate and ammonium nitrate. Inorganic salts (e.g. phosphates, magnesium sulfate, iron sulfate and copper sulfate) and vitamins may optionally be used as trace nutrient sources. Any of these components may be incorporated in a medium in any concentration that will not be detrimental to the growth of the microorganism of interest. For practical purposes, carbon sources are generally used in concentrations ranging from 0.1 to 10 wt%, preferably from 1 to 5 wt%, while nitrogen sources are in the range of 0.1 to 5 wt%, preferably 0.1 to 2 wt%. The cultivation temperature ranges from 10° to 45° C., preferably from 30° to 40° C. The medium is adjusted to a pH value in the rnage of 4–10, preferably 6–9, and cultivation is conducted by agitation culture under aeration, shake culture or stationary culture, for a period which generally lasts 3 to 14 days.

A solid medium may be prepared from wheat bran, rice hulls, rice bran or any other suitable materials that are mixed with 50–100 wt% of water. Cultivation is carried out at temperatures between 10° and 45° C., preferably between 30° and 40° C., for a period of 3–14 days. If necessary, the medium may be supplemented with suitable nitrogen sources, inorganic salts or trace nutrient sources. For mass cultivation, a liquid medium is preferred.

The culture obtained by the procedures described above has peroxidase accumulated therein. The term "culture" used here means either the cultured cells, the culture supernatant, the mixutre thereof or a culture filtrate if a liquid medium is used; if a solid medium is used, the term "culture" means the mixture of the cells and the medium on which they have grown.

For example, if a liquid medium is used, peroxidase may be recovered from the culture mixture by the following procedures. When the full growth of the organism is attained, the culture mixture is subjected to a suitable solid-liquid separation means such as cetrifugation or filtration, so as to obtain a crude enzyme solution free from the cells and insoluble matter. Peroxidase in the cells may be extracted by disrupting them by a suitable method such as grinding or ultrasonic treatment. Cells may be directly subjected to an ultrasonic treatment in a culture medium so as to disrupt the cells and a crude enzyme solution may be obtained by removing any insoluble matter from the treated solution.

If cultivation is performed on a solid medium, a crude enzyme solution may be obtained by the following procedures: water is added to the solid medium containing the cultured cells, and any insoluble matter is removed from the mixture either immediately or after disrupting the cells by a suitable means such as ultrasonic treatment.

A pure form of peroxidase may be isolated from the crude enzyme solution by conventional enzyme purification techniques, such as organic solvent fractionation, ammonium sulfate fractionation, dialysis, isoelectric precipitation and column chromatography, which may be used either independently or in combination.

The activity of the peroxidase in accordance with the present invention may be determined by the following method, wherein a 4-AA-phenol system, for example, is used as a hydrogen donor. First, 1.3 ml of 0.1% phenol solution, 0.25 ml of 0.2% 4-AA solution and 0.2 ml of 0.02% hydrogen peroxide solution are added to 1 ml of 0.1M phosphate buffer (pH, 7.0) and the mixture is prewarmed to 37° C. To the prewarmed mixture, 0.25 ml of a specific enzyme solution is added and subjected to reaction for 10 minutes. After the reaction, 0.2 ml of 20% sodium azide solution is added and the absorbance of the mixture is measured at 500 nm to obtain a reaction value, which is compared with a control value obtained by the same procedure except that the hydrogen peroxide solution is replaced by an equal volume (0.2 ml) of water. One unit (U) of peroxidase activity is indicated as the amount of oxygen that oxidizes 1 micromole of 4-AA-phenol per minute. The activity (U/ml) of peroxidase in an enzyme solution or culture solution is determined by the formula: $0.198 \times O.D._{500} \times$ (the dilution rate of the enzyme or culture solution), wherein $O.D._{500}$ is the absorbance value after subtracting the control value.

The peroxidase obtained by the present invention has the following properties.

(1) Enzyme action:

The peroxidase in accordance with the present invention catalyzes the oxidation of various compounds in the present of hydrogen peroxide by the mechanism shown below:

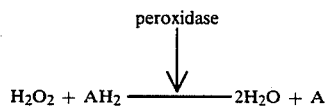

$$H_2O_2 + AH_2 \xrightarrow{\text{peroxidase}} 2H_2O + A$$

(wherein $AH_2$ is a hydrogen donor, and A is an oxidized hydrogen donor).

(2) Specificity for hydrogen donor:

The specificity of the peroxidase for a variety of hydrogen donors is shown in Table 1.

TABLE 1

| $H_2$ donor | Activity | $H_2$ donor | Activity |
|---|---|---|---|
| Phenol | +++ | Hydroquinone | + |
| Pyrogallol | +++ | p-hydroxybenzoic acid | ++ |
| p-anisidine | ++ | p-aminobenzoic acid | ++ |
| o-dianisidine | +++ | ABTS | +++ |
| guaiacol | ++ | diethylaniline | + |

(3) Optimum pH:

The optimum pH range at which the peroxidase exhibits the highest activity was checked by using samples having the same formulation as used for the assay of peroxidase activity in above (1), except that different buffers were used for different pH ranges: 0.1M acetate buffer for pH 3.5–5.5, 0.1M phosphate buffer for pH 5.5–8.0, 0.1M tris-HCl buffer for pH 7.5–9.0, and 0.1M glycine-sodium hydroxide buffer for pH 8.5–9.0. The results are summarized in FIG. 1.

Figure 2:
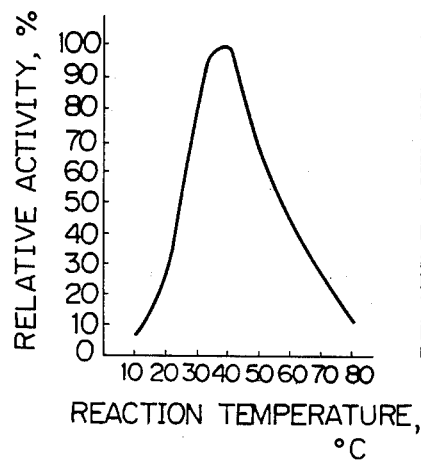
FIG. 2 is a graph showing the relationship between the reaction temperature and the relative activity of the peroxidase.

(4) Optimum working temperature:

The activity of the peroxidase was measured over the temperature range of 10°–80° C., and the results are shown in FIG. 2.

Figure 3:
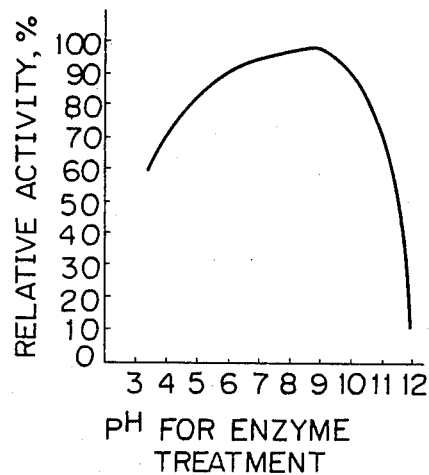
FIG. 3 is a graph showing the pH stability of the peroxidase.

(5) pH stability:

Different buffers were used for different pH ranges: 0.1M acetate buffer for pH 3.5–5.0, 0.1M phosphate buffer for pH 6.0–8.0, 0.1M tris-HCl buffer for pH 8.0–9.0, and 0.1M glycine-NaOH buffer for pH 9.0–12.0. 0.9 ml of a specific buffer solution was added to 0.1 ml of the peroxidase solution and the mixture was left to stand at 30° C. for 16 hours. The so treated enzyme solution was diluted 10-fold with 0.02M phsophate buffer (pH, 7.0) and the activity of the enzyme was measured. The results are shown in FIG. 3.

Figure 4:
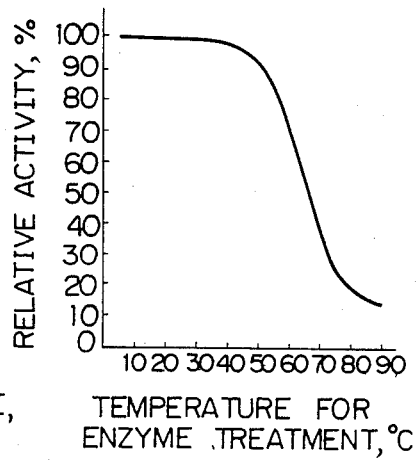
FIG. 4 is a graph showing the temperature stability of the peroxidase.

(6) Temperature stability:

Samples each prepared by adding 0.1 ml of the enzyme solution to 1.9 ml of 0.02M phosphate buffer (pH, 7.0) were held at varying temperature (20°–90° C.) for 30 minutes. Immediately thereafter, the samples were cooled with cied water for 10 minutes and residual enzyme activity in each sample was measured. The results are shown in FIG. 4.

(7) Molecular weight:

Analysis by SDS-polyacrylamide gel electrophoresis showed that the peroxidase in accordance with the present invention had a molecular weight of about 36,000.

(8) Isoelectric point:

The peroxidase was found to have an isoelectric point of 3.4 as a result of isoelectric focusing at 900 volts for 40 hours using Amphorite (Pharmacia) as a carrier (pH, 3–10).

The analytical data of the peroxidase of the invention is summarized in Table 2.

TABLE 2

| | |
|---|---|
| Sedimentation velocity ($S_{20,w}$) | 3.12 S |
| Native Mr | |
| Sedimentation equilibrium | 41,200 |
| HPLC | 41,000 |
| SDS-PAGE | 36,000 |
| Subunit Mr | |
| SDS-PAGE | 36,000 |
| Numbers of subunit | 1 |
| Prosthetic group | Protoheme IX |
| E (10 mg/ml, 1 cm, 280 nm) | 7.9 |
| pI | 3.4 |
| Sugar content | 5% |
| $K_m$ ($H_2O_2$) | 0.12 mM |
| | (2,4-DCP-4-AA) |
| Inhibitor | $CN^-$, $N_3^-$, $S_2O_4^{2-}$, $NH_2OH$ |
| | $Fe^{2+}$, $Hg^{2+}$ |
| Optimum pH | 6.0 |
| Optimum temperature | 40° C. |
| pH stability | stable at pH 5.0–9.0 |
| | (30° C., 16 hr) |
| Temperature stability | stable at 50° C. or below |
| | (pH 7.0, 30 min) |

The analytical data suggest that the peroxidase in accordance with the present invention is novel and characterized by the absence of isozymes.

Because of the absence of isozymes, this peroxidase is particularly useful as a marker enzyme in enzyme immunoassay. Thus, in place of horseradish peroxidase used in the method by Avrameas [Immunochemistry, 6, 43 (1969)], the peroxidase of the present invention may be used to label antigens or antibodies in the presence of glutaraldehyde without separating unwanted isozymes and may be used for detection or determination of antibodies or antigens.

The following Examples are provided for further illustration of the invention.

EXAMPLE 1

Ten milliliters of a medium (pH, 6.0) containing 1% glucose, 0.5% polypeptone, 0.3% yeast extract and 0.3% malt extract was put into a test tube having a diameter of 24 mm, and sterilized at 120° C. for 15 minutes. The sterilized medium was inoculated with one loopful of *Arthromyces ramosus*, which was shake-cultured on a recipro-shaker (300 rpm) at 30° C. for 8 days. The cultured mixture was filtered and the titer of peroxidase in the filtrate was found to be 10.7 U/ml.

EXAMPLE 2

Five liters of a medium (pH, 6.0) containing 1% glucose, 0.5% polypeptone and 0.3% yeast extract was charged into a 15-liter jar fermenter and sterilized by heating at 120° C. for 40 minutes. The sterilized medium was inoculated with 200 ml of a liquid preculture of

*Arthromyces ramosus.* The mixture was cultivated under aeration and agitation at 30° C. with air supplied at 0.5 vvm for 5 days. The culture mixture was filtered and the titer of peroxidase in the filtrate was found to be 3.6 U/ml.

EXAMPLE 3

Three liters of a medium having the same composition as used in Example 1 was divided into 30 equal volumes, which were distributed among the corresponding number of 500-ml culture flasks, and sterilized by heating at 120° C. for 20 minutes. A liquid preculture (10 ml) of *Arthromyces ramosus* was inoculated into each of the sterilized media and shake-cultured on a reciproshaker (110 rpm) at 28° C. for 8 days. The culture mixture was filtered to obtain a filtrate amounting to 1,915 ml. The peroxidase in this filtrate had a titer of 7.0 U/ml. To this filtrate, ammonium sulfate was added, and the fraction that precipitated at 75% saturation of ammonium sulfate was collected and dissolved in 66 ml of 0.02M phosphate buffer (pH, 7.0). The solution was dialyzed in a Cellophanne tube against the same buffer so as to remove ammonium sulfate. The dialyzate (enzyme solution) was passed through a DEAE-cellulose column equilibrated with 0.02M phosphate buffer (pH, 7.0). The absorbed fractions were eluted by a gradient of NaCl and fractions having higher activity were combined to make 106 ml. Ammonium sulfate was added and the fraction that precipitated at 75% saturation was collected. A solution of the collected precipitate in 3 ml of 0.02M phosphate buffer (pH, 7.0) containing 0.1M NaCl was dialyzed in a Cellophane tube. The dialyzate (enzyme solution) was passed through an Ultrogel ACA 44 column (LKB) equilibrated with 0.02M phosphate buffer (pH, 7.0) containing 0.1M NaCl and adsorbed fractions were eluted. Fractions having higher activity were combined to make 17 ml. Ammonium sulfate was added and the fraction that precipitated at 75% saturation was collected. The yield of the activity of the salted-out peroxidase from the culture filtrate was 57%, with the specific activity being 290 U/mg.

The peroxidase in accordance with the present invention has no isozymes present and is more suitable than the conventional peroxidase of plant origin as a clinical and diagnostic reagent or a marker enzyme in enzyme immunoassay. The peroxidase of the invention is produced from a microorganism, so it has the additional advantage of being supplied consistently in large quantities.

What is claimed is:

1. A process for producing a peroxidase comprising the following steps:

cultivating a peroxidase producing microorganisum of the strain FERM BP-838 of the genus Arthromyces characterized by the following definitions:

belonging to subdivision Deuteromycotina, class Hyphomycetes; the hypha is hyaline, septate and branched; the conidiophore is difficult to discern from a vegetative hyphae; the process of conidium formation is of thallic type; the formation of a conidium starts with the cutting off of the tip of the hypha from the base portion, ad the residual hypha is then fragmented to form a conidium; at the same time, a new hypha arises from the side of the residual hypha immediately beneath the cut plane, and another conidium forms by the same process; the conidium is a short cylinder, and hyaline;

type species: Arthromyces ramosus (FERM BP-838) N. Amano, sp. nov.;

and recovering the peroxidase accumulated in the culture.

2. A peroxidase produced by a peroxidase producing microorganism of the strain FERM BP-838 of the genus Arthromyces characterized by the following definitions:

belonging to subdivision Deuteromycotina, class Hyphomycetes;

the hypha is hyaline, septate and branched;

the conidiophore is difficult to discern from a vegetative hyphae;

the process of conidium formation is of thallic type;

the formation of a conidium starts with the cutting off of the tip of the mycelium from the base portion, and the residual hypha is then fragmented to form a conidium; at the same time, a new hypha arises from the side of the residual hypha immediately beneath the cut plane, and another conidium forms by the same process;

the condium is short and cylindrical, and hyaline;

type species: *Arthromyces ramosus* (FERM BP-838) N. Amano, sp. nov., wherein said peroxidase has the following characteristics:

optimum pH: 5–7;

optimum temperature: 30°–45° C.;

stable at pH between 5 and 10;

stable at 50° C. or below;

molecular weight as determined by SDS-polyacrylamide gel electrophoresis (PAGE): ca. 36,000;

isoelectric point (PI) as measured by isoelectric focusing (with Amphorite): pH of ca. 3.4; and absence of any isozyme.

3. A peroxidase according to claim 2 having the following characteristics:

| | |
|---|---|
| sedimentation velocity ($S_{20,w}$) | Ca. 3.12 S |
| molecular weight as determined by SDS-PAGE | Ca. 36,000 |
| sedimentation equilibrium | Ca. 41,200 |
| HPLC | Ca. 41,000 |
| subunit molecular weight as determined by SDS-PAGE | Ca. 36,000 |
| numbers of subunit | 1 |
| prosthetic group | Protoheme IX |
| E (10 mg/ml, 1 cm, 280 nm) | Ca. 7.9 |
| pI | Ca. 3.4 |
| sugar content | Ca. 5% |
| Km ($H_2O_2$) | Ca. 0.12 mM (2,4-DCP-4-AA) |
| inhibited by | $CN^-$, $N_3^-$, $S_2O_4^{2-}$, $NH_2OH$, $Fe^{2+}$, $Hg^{2+}$ |
| optimum pH | Ca. 6.0 |
| optimum temperature | Ca. 40° C. |
| pH stability | stable at pH 5.0–9.0 (30° C., 16 hr) |
| temperature stability | stable at 50° C. or below (pH 7.0, 30 min) |
| absence of any isozyme. | |

* * * * *